United States Patent [19]

Miwa et al.

[11] 4,371,615
[45] Feb. 1, 1983

[54] METHOD FOR STABILIZING THE CHARACTERISTICS OF MICROORGANISM CONTAINING A PLASMID

[75] Inventors: Kiyoshi Miwa, Matsudo; Haruo Momose, Kamakura, both of Japan

[73] Assignee: Ajinomoto Company Incorporated, Tokyo, Japan

[21] Appl. No.: 152,633

[22] Filed: May 23, 1980

[30] Foreign Application Priority Data

May 23, 1979 [JP] Japan .................................. 54-63467

[51] Int. Cl.³ ...................... C12P 13/08; C12N 15/00; C12R 1/85; C12R 1/19
[52] U.S. Cl. ................................... 435/115; 435/172; 435/253; 435/317; 435/848; 435/849
[58] Field of Search ............... 435/106, 115, 172, 235, 435/253, 317, 848, 849

[56] References Cited

U.S. PATENT DOCUMENTS

| | | | |
|---|---|---|---|
| 3,622,453 | 11/1971 | Akeyama et al. | 435/849 |
| 3,684,654 | 8/1972 | Nakayama et al. | 435/849 |
| 3,923,603 | 12/1975 | Clakrabarty et al. | 435/172 |
| 4,190,495 | 2/1980 | Curtiss | 435/172 |
| 4,237,224 | 12/1980 | Cohen et al. | 435/68 |
| 4,304,863 | 8/1981 | Collins | 435/172 |
| 4,321,325 | 3/1982 | Debabov et al. | 435/172 |

OTHER PUBLICATIONS

Cossart et al, Molec. gen. Genet. "Construction and Expression of a Hybrid Plasmid Containing *Escherichia coli:* thr A and thr B Genes", *Chem. Abstracts* vol. 91, No. 21, p. 346 (1979) Abs. No. 171480g.
Newcombe et al, "Spontaneous Mutation to Streptomycin Resistance and Dependence in *Escherichia coli*", *J. Bact.,* vol. 57, (1949), pp. 565–572.
Hedges et al, "R Factors Conferring Resistance to Trimethopan but not Sulphonamides", *J. Gen. Microbiol.,* vol. 73, (1972), pp. 573–575.
Staudenbauer, "Structure and Replication of the Colicin el Plasmid", *Current Topics in Microbiology and Immunology,* 83, (1978), pp. 107–111.
Bolivar et al, "Construction and Characterization of New Cloning Vehicles II A Multipurpose Cloning System", *Chem. Absts.,* vol. 88, No. 17, p. 255 (1978), Abs. No. 117616p.
Bolivar, "Construction and Characterization of new Cloning Vehicles III; Derivatives of plasmid pBR 322 carrying unique EcoRI sites for selection of ERI Generated Recombinant DNA Molecules"; *Chem. Absts.* vol. 90, No. 9, p. 246 (1979), Abs. No. 68970e.
Dr. P. Cossart, Molec. Gen. Genet. 175, 39–44 (1979) Construction and Expression of a Hybrid Plasmid Containing the *Escherichia coli* thr A and thr B Genes.
C. Weissman, vol. 261, 6/3/76 pp. 428–429, "Reduction of Possible Hazards in the Preparation of Recombinant Plasmid DNA".
J. Collins: Curr. Top. Microbiol. Immunol., vol. 78, 1977, pp. 121–170, "Gene Cloning with Small Plasmids".
H. Momose et al, *Genetics,* 67:19–38 Jan. 1971.

*Primary Examiner*—Thomas G. Wiseman
*Attorney, Agent, or Firm*—Oblon, Fisher, Spivak, McClelland & Maier

[57] ABSTRACT

A streptomycin dependent mutant of a microorganism of the genus Escherichia which contains a plasmid containing genetic information controlling streptomycin independence maintains its properties when cultured in a medium devoid of streptomycin. The plasmid may also contain genetic information controlling the production of a chemical compound by the microorganism. Fermentation cultures of such microorganisms in media devoid of streptomycin do not lose their industrially desirable ability to synthesize useful compounds.

8 Claims, No Drawings

METHOD FOR STABILIZING THE CHARACTERISTICS OF MICROORGANISM CONTAINING A PLASMID

BACKGROUND OF THE INVENTION

1. Field of the Invention

This invention relates to a method for stabilizing the characteristics of a microorganism containing a plasmid (plasmid-having microorganism).

2. Description of the Prior Art

Attempts have been made to produce useful microorganisms by transforming Escherichia strains by inserting a plasmid which incorporates useful genetic information.

However, in general, the plasmid may be eliminated during culturing, so that the microbial characteristics controlled by the plasmid become unstable in the microbial cell population. This phenomenon restricts the commercial application of the plasmid-containing microorganisms.

Such instability can be diminished if the plasmid-containing cells alone survive, while the plasmid-free cells, arising by the above-mentioned phenomenon, are selectively killed.

Attempts have been made to produce this selective killing of cells which do not contain the desired plasmid by using a plasmid which incorporates one or more genes which endow the cell with resistance to antibiotics. The cells are then cultured in a medium containing the antibiotic(s) corresponding to the resistance factors conferred by the plasmid. In such a medium, only the cells which contain the plasmid can survive, since they alone have the ability to resist the antibiotic(s). If the cells lose the plasmid containing the commercially useful genes, they also lose their antibiotic resistance and succumb to the action of the antibiotics which are present in the culture medium. This method, however, suffers from the drawback that relatively large amounts of antibiotic must be used, and therefore it is not well adapted to industrial exploitation.

Hence, a need has continued to exist for a method of assuring the stability of a culture of microorganisms containing an industrially useful plasmid which is effective, economical, and adapted to industrial practice.

SUMMARY OF THE INVENTION

Accordingly, it is an object of this invention to provide a microorganism containing a plasmid which provides the microorganism with industrially useful capabilities.

A further object is to provide a microorganism culture wherein microorganisms containing an industrially useful plasmid survive while those microorganisms which do not contain such a plasmid are selectively killed.

A further object is to provide a plasmid which is capable of conferring on a microorganism an industrially useful property and a property which enables it to survive only under limited conditions of culture.

Further objects of the invention will become apparent from the description of the invention which follows.

The inventors have succeeded in genetically constructing a microorganism of the genus Escherichia by introducing into a mutant species whose growth is dependent on streptomycin (streptomycin dependent mutant) a plasmid incorporating a chromosomal DNA fragment of Escherichia which controls independence from steptomycin (streptomycin independent gene). The growth of the newly constructed microorganism is not dependent on streptomycin, and therefore, it can grow in a culture medium free of streptomycin. However, if the plasmid should be eliminated from the cell, the microorganism becomes dependent on streptomycin and cannot grow in a culture medium devoid of streptomycin. Therefore in a culture of cells of the novel microorganism of this invention, wherein the culture medium does not contain streptomycin, if any of the cells should lose the plasmid which gives them their industrially useful properties, they would simultaneously lose their ability to survive without the presence of streptomycin and would therefore be eliminated from the culture. In this way the stability of the culture with respect to the industrially useful properties of the microorganisms is maintained, even without the addition of antibiotics to the culture medium. Consequently, the microorganism and method of this invention are of great utility in commercial fermentation processes.

DESCRIPTION OF THE PREFERRED EMBODIMENTS

The streptomycin dependent mutant used in preparing the microorganism of this invention cannot grow in a culture medium without streptomycin, and was reported by Newcombe et al (Genetics 35 603 (1950)). These mutants are sometimes dependent on paromomycin, kanamycin or ethanol (Genetics 67 19–38 (1971)), and therefore the streptomycin dependent mutants of this invention include those dependent on paromomycin, kanamycin or ethanol together with those dependent on streptomycin.

To obtain the streptomycin independence gene from a microorganism, whose growth is independent of streptomycin, chromosomal DNA is extracted by conventional procedures and treated with a restriction endonuclease.

As the vector DNA, any plasmid or phage which can propagate in microbial cells of Escherichia can be employed. No special method is required to insert the chromosomal DNA fragment into the vector; any conventional technique used in preparing recombinant DNA may be used. The hybrid plasmid thus obtained can be incorporated into a microorganism of the genus Escherichia by conventional transformation techniques, although the efficiency may differ among these techniques.

Transformants are easily selected since these colonies can grow on a medium without streptomycin and have a marker in the vector used such as ampicillin resistance.

When the plasmid in a transformant thus obtained carries genetic information useful for a fermentation process together with the streptomycin independent gene, the transformant maintains a high productivity during the fermentation because the characteristics of the microorganisms controlled by the plasmid are stably maintained in the medium devoid of streptomycin.

Having generally described the invention, a more complete understanding can be obtained by reference to certain specific examples, which are provided herein for purposes of illustration only and are not intended to be limiting unless otherwise specified.

EXAMPLE 1

In order to obtain a microorganism which can maintain a plasmid stably, a streptomycin independence gene of strain No. 4-R (NRRL B-12266), a streptomycin resistant mutant derived from *Escherichia coli* K-12 (ATCC 10798), was introduced by cloning into strain No. 4-D (NRRL B-12267), a streptomycin dependent mutant, by the following procedure:

(1) Preparation of chromosomal DNA having genetic information for streptomycin independence:

No. 4-R was cultured at 37° C. for 3 hours with shaking in one liter of L-medium containing 1 g/dl peptone, 0.5 g/dl yeast extract, 0.1 g/dl glucose and 0.5 g/dl NaCl (pH was adjusted to 7.2). Cells of the exponential growth phase were harvested, and the chromosomal DNA was extracted from the cells by the conventional phenol method, which yielded 2.4 mg purified DNA.

(2) Preparation of vector DNA:

In order to clone the chromosomal region specifying the streptomycin independent character, DNA of plasmid pBR 322, a DNA vector possessing ampicillin resistant ($Ap^r$) and tetracycline resistant ($Tc^r$) genes as two genetic markers, was prepared as follows:

A strain of *Escherichia coli* K-12 containing pBR 322 was cultured at 37° C. in a medium containing 2 g glucose, 1 g $NH_4Cl$, 6 g $Na_2HPO_4$, 3 g $KH_2PO_4$, 5 g NaCl, 0.1 g $MgSO_4.7H_2O$, 0.15 g $CaCl_2 2H_2O$, 20 g "Casamino acid" (casein-hydrolysate), 0.05 g L-tryptophan, 0.05 g thymine, 100 μg thiamine.HCl and 170 μg/ml chloramphenicol, per liter, (pH was adjusted to 7.2), whereby plasmid pBR 322 was multiplied and accumulated in the cell. After 16 hours of the cultivation, cells were harvested and lysed by treatment with lysozyme and SDS. Then, the lysate was subjected to ultra-centrifugation (30,000×g) for one hour. The supernatant was then concentrated, and finally 580 μg of the plasmid DNA was obtained by the cesium chloride-ethidium bromide equilibrium density gradient centrifugation method.

(3) Insertion of chromosomal DNA fragment into vector:

Ten micrograms each of the chromosomal DNA and the vector DNA obtained in steps (1) and (2) were treated with restriction endonuclease Bam HI at 37° C. for one hour to cleave the DNA chains. Each of the reaction mixtures was heated at 65° C. for 5 minutes, and then both were mixed together. To the combined reaction mixture was added ATP, dithiothreitol and $T_4$ phage DNA ligase; the mixture was heated at 10° C. for 24 hours, and then heated at 65° C. for 5 minutes. Two volumes of ethanol were added to one volume of the reaction mixture to obtain precipitated DNA.

(4) Genetic transformation with the plasmid carrying genetic information specifying streptomycin independence:

Streptomycin dependent strain No. 4-D derived from *E. coli* K-12 was cultured at 37° C. with shaking in 10 ml of L-medium to which 100 μg/ml of streptomycin was added. In the middle stage of the exponential growth phase, cells were harvested and suspended in 0.1 M $MgCl_2$ and 0.1 M $CaCl_2$ solutions in that order, whereby "competent" cells having the ability to take up DNA were prepared.

To the competent cell suspension, a solution of the DNA obtained in step (3), which includes the plasmid DNA incorporating the streptomycin independent gene, was added, and the mixture was kept in an ice bath for 30 minutes, then heated at 42° C. for 2 minutes, and again allowed to stand in an ice bath for 30 minutes to complete the incorporation of DNA into the cells.

A certain portion of the cell suspension was put into the L-medium containing 100 μg/ml streptomycin, and incubated at 37° C. for 2 hours with shaking. Thus, the transformation reaction was completed.

The cells were harvested, washed and resuspended. The cell suspension was then spread onto agar plates without streptomycin, and incubated at 37° C. After 2 days of incubation, six colonies appeared on the plate, and all the colonies were picked up and purified.

The transformants thus obtained were streptomycin independent and ampicillin resistant and were therefore, different from the recipient strain No. 4-D. This means that only the cells incorporated with new hybrid plasmid, composed of pBR 322 and the chromosomal region specifying streptomycin independence, have the selective advantage and grew as streptomycin-independent, ampicillin-resistant colonies.

(5) Stability of the transformant obtained:

Using AJ 11346 (FERM-P 4949 NRRL B-12111) selected from the transformants obtained in step (4), the genetic stability of the ampicillin resistant character was tested and the results are shown in the following table.

The stability test was carried out by subculturing the test strain sequentially four times at 40° C. on two series of agar plates: one is L-medium supplemented with 100 μg/ml of streptomycin and another is L-medium without streptomycin. After the four transfers from plate to plate, colonies were isolated using the same series of agar plates, respectively, and these colonies were then tested with 100 μg/ml of ampicillin (without streptomycin). As the control, strain No. 4-R (pBR 322+) was used, which was constructed by introducing the original vector pBR 322 (including ampicillin resistance gene, but not streptomycin independence gene) into strain No. 4-R.

As can be seen in Table 1, the genetic character of ampicillin resistance in AJ 11346 was remarkably stable when streptomycin was absent compared with in No. 4-R (pBR 322+).

TABLE 1

| Strain Tested | Streptomycin | Colonies Having Resistance to Ampicillin (%) Number of Times of Subculturing | | | |
|---|---|---|---|---|---|
| | | 1 | 2 | 3 | 4 |
| AJ 11346 | Not added | 100 | 100 | 100 | 100 |
| AJ 11346 | Added | 93 | 79 | 29 | 0 |
| No. 4-R (pBR 322+) | Not added | 96 | 85 | 40 | 26 |

EXAMPLE 2

A threonine-producing microorganism containing a plasmid having two different chromosomal regions incorporated, one related to threonine production and another specifying the streptomycin independence, was obtained using streptomycin dependent strain No. 4-D (pro−, thiamine−, ile−, met− AHV(α-amino-β-hydroxy-valeric acid)$^r$, (streptomycin)$^d$) which is a derivative of *Escherichia coli* K-12, *Escherichia coli* AJ 11335 (FERM-P 4901, NRRL B-12100) containing a plasmid having a chromosomal region controlling threonine production (hereinafter this plasmid is referred to as "threonine-plasmid"), and *Escherichia coli* AJ 11346 shown in Example 1, by the following procedure:

(1) Preparation of *Escherichia coli* AJ 11335:

(a) Preparation of chromosomal DNA possessing genetic information responsible for high production of L-threonine.

Strain AJ 11332 (FERM-P 4898, NRRL B-12097) (pro$^-$, thiamine$^-$, ile$^-$, met$^-$, AHV$^r$) was cultured at 37° C. for 3 hours with shaking in 1 l of L-medium containing 1% peptone, 0.5% yeast extract, 0.1% glucose and 0.5% NaCl, and adjusted to pH 7.2, and bacterial cells in exponential growth phase were collected. Chromosomal DNA was extracted by the conventional phenol method, and 5.3 mg of purified DNA were obtained.

(b) Preparation of vector DNA:

For the purpose of cloning the gene controlling the high production of L-threonine (threonine operon containing mutation point of AHV resistance), DNA of plasmid pBR 322, a vector containing both ampicillin and tetracycline resistance genes as markers, was prepared as follows:

A strain of *Escherichi coli* K-12 containing the plasmid pBR 322 was incubated at 37° C. in 1 l of a glucose—"casamino acid"—inorganic salts medium to which 170 µg/ml of chloramphenicol had been added. The glucose—"casamino acid"—inorganic salts medium contained 2 g glucose, 1 g NH$_4$Cl, 6 g Na$_2$HPO$_4$, 3 g KH$_2$PO$_4$, 5 g NaCl, 0.1 g MgSO$_4$.7H$_2$O, 0.015 g CaCl$_2$.2H$_2$O, 20 g "casamino acid", 0.05 g L-tryptophan, 0.05 g thymine and 100 µg thiamine.HCl, per liter, and the pH was adjusted to 7.2. Through this process, the plasmid DNA was multiplied and accumulated abundantly in the bacterial cells.

After 16 hours of the incubation, the cells were harvested and then lysed by treatment with lysosyme and SDS. The lyzate was centrifuged at 30,000×g for 1 hour to obtain supernatant. After concentrating the supernatant, 580 µg of the plasmid DNA was obtained by fractionation using cesium chloride-ethidium bromide equilibrium density gradient centrifugation.

(c) Insertion of chromosomal DNA fragment into vector:

Ten microgram portions of the chromosomal DNA and the vector DNA were each treated with restriction endonuclease Hind III at 37° C. for 1 hour to cleave DNA chains, and then heated at 65° C. for 5 minutes.

The digested chromosomal DNA solution and vector DNA solution were mixed and subjected to the ligation reaction of DNA fragments by the T$_4$ phase DNA ligase in the presence of ATP and dithiothreitol at 10° C. for 24 hours. The reaction mixture was then heated at 65° C. for 5 minutes, and twice its volume of ethanol was added to it. The thus precipitated recombinant DNA was recovered.

(d) Genetic transformation with the hybrid plasmid containing the genetic information of high threonine productivity:

An L-threonine-requiring strain of *Escherichia coli* No. 255 (NRRL B-12265), which was derived from threonine-producing strain AJ 11332 by N-methyl-N'-nitro-N-nitrosoguanidine mutagenesis, was cultured in 10 ml of L-medium at 37° C. with shaking. Cells in the exponential growth phase were harvested, and suspended in 0.1 M MgCl$_2$ solution and then in 0.1 M CaCl$_2$ solution in an ice bath, whereby "competent" cells having the ability to take up DNA were prepared.

To the suspension of competent cells the DNA obtained in step (c), which contains the hybrid plasmid DNA, was added. The suspension was kept in an ice bath for 30 minutes, then heated at 42° C. for 2 minutes, and again allowed to stand in an ice bath for 30 minutes. The cells, now containing the DNA, were inoculated into L-medium and the medium was shaken at 37° C. for 2 hours, whereby the transformation reaction was completed. The cells were collected, washed, and resuspended. A small portion of the cell suspension was spread on an agar plate containing 2 g glucose, 1 g (NH$_4$)$_2$SO$_4$, 7 g K$_2$HPO$_4$, 2 g KH$_2$PO$_4$, 0.1 g MgSO$_4$.7H$_2$O, 0.5 g sodium citrate.2H$_2$O, 20 mg ampicillin, 100 mg L-proline, 100 mg L-isoleucine, 100 mg L-methionine, 1 mg thiamine.HCl and 2 g agar, per liter (pH was adjusted to 7.2). The plate was incubated at 37° C. After 3 days incubation, 21 colonies appeared on the plate. All of the colonies were picked up, purified and isolated.

Every transformant thus obtained did not require L-threonine and was resistant to ampicillin. Thus, they were apparently different in character from strain No. 255 which was the recipient.

Threonine-producing strain AJ 11334 (FERM-P 4900, NRRL B-12099) was obtained thus as the transformant containing the threonine-plasmid.

The threonine plasmid in AJ 11334 was isolated by a method similar to step (b), and incorporated into the parent strain AJ 11332 by a transformation technique analogous to that described in step (d). The transformant AJ 11335 (FERM-P 4901, NRRL B-12100) was selected as an ampicillin resistant colony.

(2) Preparation of threonine plasmid and plasmid integrated streptomycin independent gene:

The DNA of the threonine plasmid and the plasmid integrated with streptomycin independence gene were extracted from AJ 11335 and AJ 11346, respectively, by the procedure described in step (2) of Example 1.

(3) In vitro DNA recombination:

The plasmid DNAs obtained in step (2) were mixed and treated with restriction endonuclease Bam HI at 37° C. for 2 hours to cleave the DNA chains, and then heated at 65° C. for 5 minutes. The cleaved DNA chains were recombined by the action of DNA ligase in the presence of ATP. By adding two volumes of ethanol, the hybrid DNAs were precipitated.

(4) Transformation using plasmid DNA having both the threonine-producing gene and the streptomycin independence gene:

Strain No. 4-D was made "competent" in the manner described in step (4) of Example 1. The competent cells were subjected to the transformation reaction using the DNA preparation obtained in step (2), the cells were then spread onto a plate of L-medium containing 20 µg/ml ampicillin, and cultured at 37° C. After 2 days of the cultivation, 1000 colonies appeared on the plate, and the colonies were replicated onto a plate of minimum medium on the whole surface of which threonine-requiring mutant cells of *Escherichia coli* K-12 had been spread.

The transformant colonies which excrete threonine into the plate during the cultivation were screened by detecting growth halos of the threonine-requiring mutant cells around each colony. One colony was recognized as a very good threonine excreter, and was picked up and purified.

The strain AJ 11354 (FERM-P 4987, NRRL B-12112) thus obtained was independent of streptomycin and capable of producing a large amount of threonine.

(5) Production of L-threonine by the novel threonine producing strain:

Table 2 shows the experimental result of the fermentative production of L-threonine using strain AJ 11354.

The cultivation medium contained 3 g/dl glucose, 1 g/dl (NH$_4$)$_2$SO$_4$, 0.1 g/dl KH$_2$PO$_4$, 0.1 g/dl MgSO$_4$·7H$_2$O, 10 mg/dl FeSO$_4$·7H$_2$O, 10 mg/dl MnSO$_4$·4H$_2$O, 1 mg/l thiamine-HCl, 450 mg/l L-proline, 100 mg/l L-isoleucine, 100 mg/l L-methionine, 100 mg/dl L-aspartic acid, 4 g/dl CaCO$_3$, and was adjusted to pH 7.0 with KOH. Twenty ml portions of the medium were put into 500 ml flasks, inoculated with AJ 11334, and held for 68 hours at 30° C. with shaking.

As a comparison, AJ 11335 was cultured in the same manner, and the yield tabulated in Table 2.

TABLE 2

| Microorganism Used | L-threonine Produced (g/dl) |
|---|---|
| AJ 11354 | 1.21 |
| AJ 11335 | 1.12 |

Threonine was determined by a conventional microbiological assay.

In the culture liquid of AJ 11335, about 20% of the cells had lost their plasmid, while, in the culture liquid of AJ 11354, no plasmid-free cell was found.

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A method for stabilizing the characteristics of a microorganism containing a plasmid, which comprises:
    introducing a plasmid obtained from a microorganism of the genus Escherichia into a mutant of the genus Escherichia, said plasmid having incorporated therein a chromosomal DNA fragment expressing independence of streptomycin, and the growth of said mutant being dependent on streptomycin; and
    cultivating and maintaining the stability of said plasmid containing microorganism in a growth medium free of streptomycin.

2. The method of claim 1, wherein said mutant belongs to the species *Escherichia coli*.

3. The method of claim 1, wherein said microorganism belongs to the species *Escherichia coli*.

4. The method of claim 1, wherein said plasmid is pBR 322.

5. The method of claim 1, wherein said plasmid further contains genetic information controlling the production of a chemical compound by said microorganism.

6. The method of claim 5, wherein said compound is threonine.

7. The method of claim 5, wherein said genetic information is in the form of a chromosomal fragment obtained from a microorganism of the genus Escherichia.

8. A method for stabilizing the characteristics of a microorganism containing a plasmid, which comprises:
    introducing a plasmid obtained from a microorganism of the genus Escherichia into a mutant of the genus Escherichia, said plasmid having incorporated therein a chromosomal DNA fragment expressing independence of streptomycin and a chromosomal DNA fragment expressing threonine production, and the growth of said mutant being dependent on streptomycin; and
    cultivating and maintaining the stability of said plasmid containing microorganism in a growth medium free of streptomycin.

* * * * *